(12) United States Patent
Sternå et al.

(10) Patent No.: US 11,590,710 B2
(45) Date of Patent: Feb. 28, 2023

(54) 3D BIOPRINTERS, A 3D BIOPRINTING TOOLHEAD AND A METHOD FOR 3D BIOPRINTING A CONSTRUCT

(71) Applicant: Cellink Bioprinting AB, Gothenburg (SE)

(72) Inventors: Erik Sternå, Mölndal (SE); Jockum Svanberg, Gothenburg (SE); Erik Gatenholm, Gothenburg (SE); Hector Martinez, Gothenburg (SE)

(73) Assignee: Cellink Bioprinting AB, Gothenburg (SE)

( * ) Notice: Subject to any disclaimer, the term of this patent is extended or adjusted under 35 U.S.C. 154(b) by 431 days.

(21) Appl. No.: 16/477,316

(22) PCT Filed: Jan. 10, 2018

(86) PCT No.: PCT/SE2018/050017
§ 371 (c)(1),
(2) Date: Jul. 11, 2019

(87) PCT Pub. No.: WO2018/132057
PCT Pub. Date: Jul. 19, 2018

(65) Prior Publication Data
US 2019/0375163 A1 Dec. 12, 2019

Related U.S. Application Data

(60) Provisional application No. 62/445,862, filed on Jan. 13, 2017.

(30) Foreign Application Priority Data

Jan. 13, 2017 (SE) .................................. 1750027-3

(51) Int. Cl.
*B29C 64/393* (2017.01)
*B33Y 10/00* (2015.01)
(Continued)

(52) U.S. Cl.
CPC ............ *B29C 64/393* (2017.08); *B29C 64/20* (2017.08); *B33Y 10/00* (2014.12); *B33Y 30/00* (2014.12);
(Continued)

(58) Field of Classification Search
None
See application file for complete search history.

(56) References Cited

U.S. PATENT DOCUMENTS

| 2006/0160250 A1 | 7/2006 | Bonassar et al. |
| 2007/0026102 A1 | 2/2007 | Devos et al. |

(Continued)

FOREIGN PATENT DOCUMENTS

| CN | 205416371 U | 8/2016 |
| WO | WO 2014/149141 A1 | 9/2014 |

(Continued)

OTHER PUBLICATIONS

An, Jia et al.: "Design and 3D Printing of Scaffolds and Tissues", *Engineering*, Jun. 2015, vol. 1, Issue 2, pp. 261-268.

(Continued)

*Primary Examiner* — Robert J Grun
(74) *Attorney, Agent, or Firm* — McCarter & English, LLP

(57) ABSTRACT

The present disclosure relates to a 3D bioprinter (1) comprising a base unit (2). The base unit (2) has a support (3) adapted for mounting of at least one toolhead (4), a communication interface part (5) for communication of data with the at least one toolhead (4), when mounted, and a base unit processing element (7) adapted to communicate with a toolhead processing element (8) of the at least one toolhead over said communication interface part (5). The present disclosure relates further to a 3D bioprinter toolhead. The present disclosure relates further to a method for bioprinting a construct.

10 Claims, 3 Drawing Sheets

(51) Int. Cl.
　　　*B33Y 30/00*　　(2015.01)
　　　*B33Y 50/02*　　(2015.01)
　　　*B33Y 70/00*　　(2020.01)
　　　*B29C 64/20*　　(2017.01)
　　　*C12M 3/00*　　(2006.01)
　　　*C12N 5/00*　　(2006.01)
　　　*C12M 1/26*　　(2006.01)
　　　*B33Y 40/00*　　(2020.01)
　　　*B29L 31/00*　　(2006.01)

(52) U.S. Cl.
　　　CPC ............... *B33Y 40/00* (2014.12); *B33Y 50/02* (2014.12); *B33Y 70/00* (2014.12); *C12M 21/08* (2013.01); *C12M 33/00* (2013.01); *C12N 5/0062* (2013.01); *B29K 2995/0056* (2013.01); *B29L 2031/7532* (2013.01); *C12N 2513/00* (2013.01)

(56) References Cited

U.S. PATENT DOCUMENTS

| | | |
|---|---|---|
| 2013/0180450 A1 | 7/2013 | Hamilton et al. |
| 2015/0140058 A1 | 5/2015 | Tumey et al. |
| 2015/0174824 A1 | 6/2015 | Gifford et al. |
| 2016/0039148 A1 | 2/2016 | Marino |
| 2016/0095959 A1 | 4/2016 | Bonassar et al. |
| 2016/0303796 A1 | 10/2016 | Bredt et al. |
| 2018/0326660 A1* | 11/2018 | Gifford ................ B29C 64/209 |

FOREIGN PATENT DOCUMENTS

| | | |
|---|---|---|
| WO | WO 2015/038072 A1 | 3/2015 |
| WO | WO 2015/054577 A1 | 4/2015 |

OTHER PUBLICATIONS

Blacksmith Genesis: Our Story You-Tube, https://www.youtube.com/watch?v=oP_sY5fk3L0, accessed Jul. 10, 2019.

International Search Report and Written Opinion prepared by the European Patent Office, acting as the ISA, for corresponding international application PCT/SE2018/050017 dated Apr. 20, 2018.

Swedish Search Report prepared for priority application, SE 1750027-3, dated Aug. 21, 2017, English translation.

Office action prepared by Swedish Patent Office for priority application SE 1750027-3 dated Mar. 13, 2018, English translation.

Office action prepared by Swedish Patent Office for priority application SE 1750027-3 dated Dec. 4, 2018, English translation.

Song, Yu; "Overview of 3d Bioprinting Technology: Imaging Technology and Printing Technology", *Advanced Materials Industry*, No. 1, Jan. 5, 2017, pp. 20-25, with English summary.

* cited by examiner

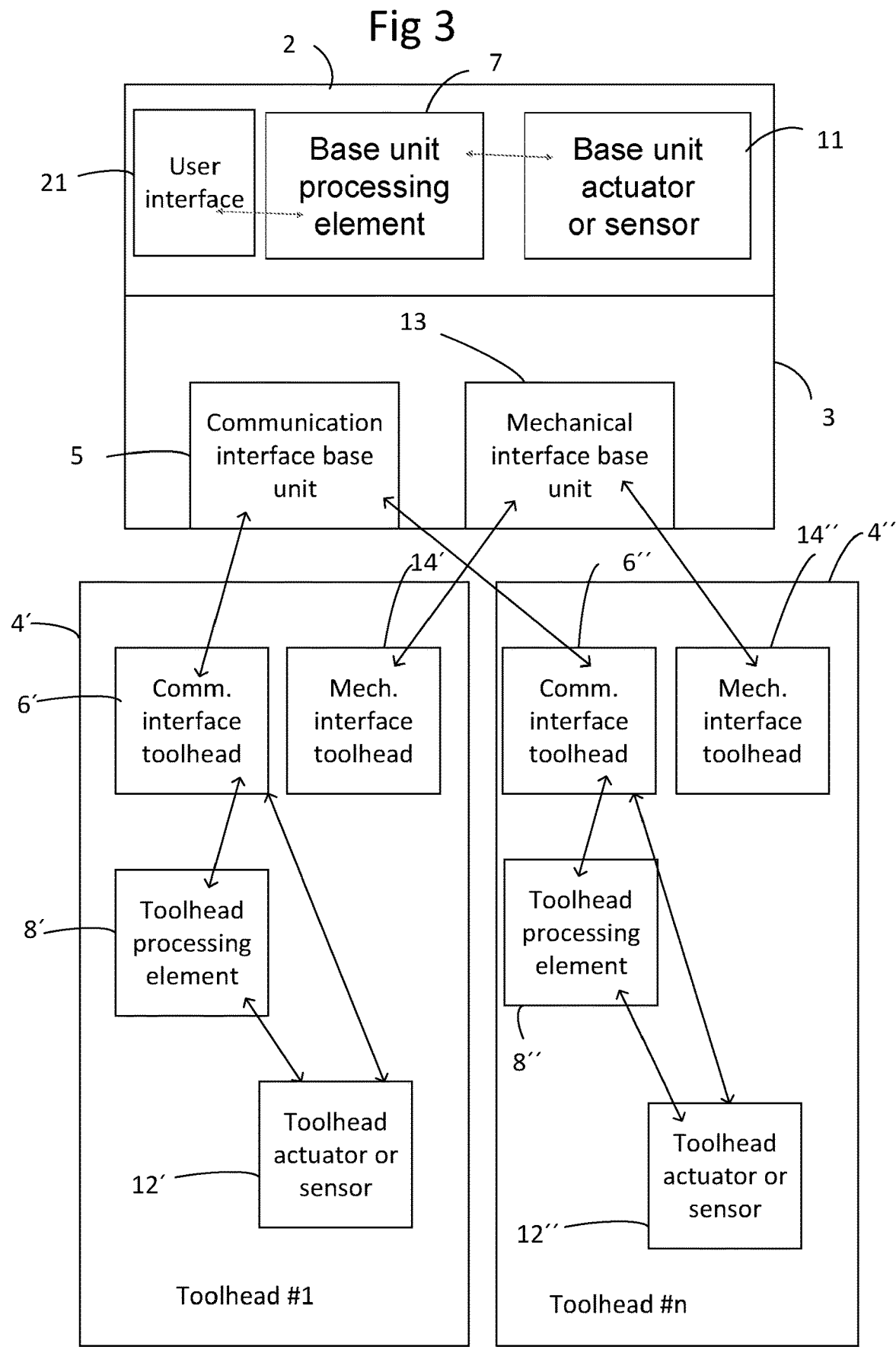

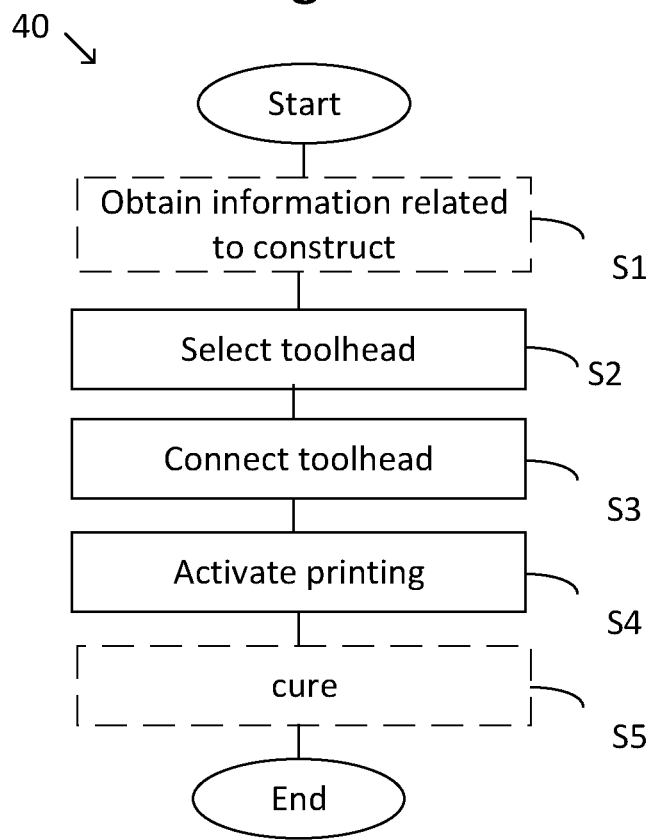
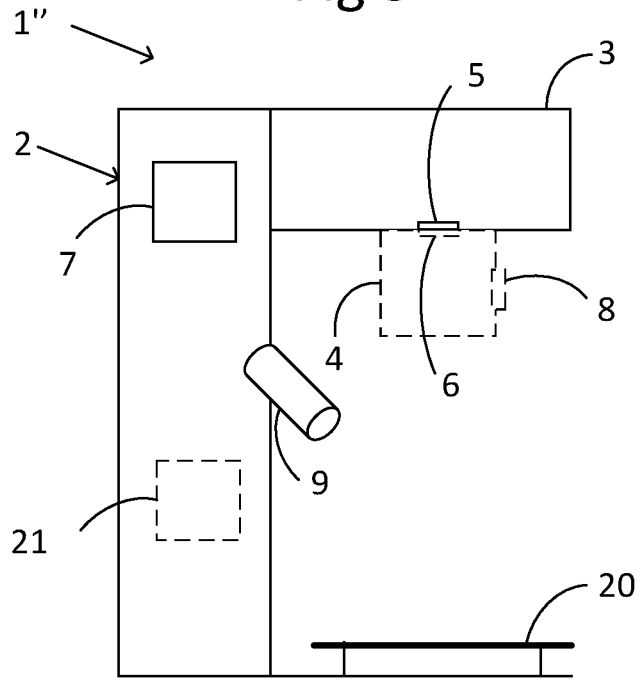

3D BIOPRINTERS, A 3D BIOPRINTING TOOLHEAD AND A METHOD FOR 3D BIOPRINTING A CONSTRUCT

CROSS-REFERENCE TO RELATED APPLICATIONS

This application is the National Stage entry under 35 U.S.C. § 371 of International Application Number PCT/5E2018/050017 filed on Jan. 10, 2018, published on Jul. 19, 2018 under publication number WO 2018/132057 A1, which claims the benefit of priority under 35 U.S.C. § 119 of Swedish patent application number 1750027-3 filed Jan. 13, 2017 and U.S. Provisional Patent Application Ser. No. 62/445,862 filed Jan. 13, 2017.

TECHNICAL FIELD

The present disclosure relates to a 3D bioprinter comprising a base unit having a support for mounting of at least one toolhead.

The present disclosure further relates to a method for bioprinting a construct.

BACKGROUND ART

Bioprinting, an additive manufacturing technology, has gained due attention for its ability to spatially control the placement of cells, biomaterials and biological molecules. Consequently, it offers endless possibilities to the future of tissue and organ regeneration, basic research and drug screening. The 3D bioprinter is able to dispense materials while moving in X, Y, and Z directions, which enables the engineering of complex structures from the bottom up. Moreover, this technology allows the biofabrication of biomimetic-shaped 3D structures unique to the target tissue or organ, since it can be combined with CAD/CAM technology using patients' medical images. The development of hydrogel bioinks with good printability and bioactive properties that guide cellular fate processes would contribute to translation of this promising technology into the clinic. Hydrogels based on natural polymers are known for their favorable biocompatible properties and are attractive biomaterials for cell encapsulation. They provide an aqueous 3D environment with biologically relevant chemical and physical signals, mimicking the natural extracellular matrix environment.

SUMMARY

One object of the invention is to obtain 3D bioprinters which are improved over known 3D bioprinters.

The present disclosure relates to a 3D bioprinter. The 3D bioprinter comprises a base unit comprising a support adapted for mounting of at least one toolhead, a communication interface part for communication of data with the at least one toolhead, when mounted, and a base unit processing element (7) adapted to communicate with a toolhead processing element of the at least one toolhead over said communication interface part.

The toolhead processing element may have storing capacity. The toolhead processing element is capable of transmitting and/or receiving analog or digital data. The toolhead processing element may also have processing capacities so as to perform calculations. Thus, the toolhead has intelligence.

Thus, as the toolhead has a toolhead processing element, the need for manual user input related to the toolhead can be reduced or eliminated. The possible burdensome manual user input which can be avoided/reduced include for example type, dimension, and other characteristics of the toolhead. This makes it easier and faster to use the 3D bioprinter. This in turn removes the risk of manual input of erroneous information related to the toolhead.

Further, the toolhead processing element may collect data related to the toolhead, for example obtained by the toolhead itself or sensors mounted thereon or in association therewith. The toolhead processing element can then be arranged to format the collected data to a format appropriate for the 3D bioprinter and to transmit the data in the appropriate format to the communication interface part of the 3D bioprinter. This facilitates integration between the 3D bioprinter and toolhead, if the toolhead has to be substituted. This is particularly advantageous for exchangeable toolheads.

Further, if the toolhead processing element has processing capacities it can be arranged to at least partly control operation of its toolhead or other equipment such as another toolhead and/or an exhaust for gas. One advantage with having this functionality at the toolhead is that software within the 3D bioprinter does not have to be amended and updated when updated toolheads are mounted to the 3D bioprinter.

With this solution the base unit processing element can act as master and the toolhead processing element can act as slave, and vice versa.

In different embodiments, the support comprises a support part adapted for mounting of at least one exchangeable toolhead.

Thereby the 3D bioprinter becomes very flexible and efficiency in operation of the 3D bioprinter can be increased. For example, the user can prepare the toolhead outside the 3D bioprinter, wherein the preparation may for example involve loading material and/or selecting needle. Then the currently used toolhead can be substituted with the one currently used.

Thereby the bioprinter does not need to be stopped for time consuming activities such as loading of material and/or changing needle. Instead, a short stop can be made to substitute the currently used toolhead with the prepared one. Alternatively, the currently used toolhead can be exchanged when printing. For example, if the support is adapted to mount a plurality of toolheads, the exchange can easily be done while printing.

Detection of a new toolhead can be done automatically by the 3D bioprinter or it can be set by the user.

The toolhead can be inserted or removed by the user with our without use of a tool. Alternatively, the toolhead can be inserted and/or removed by the 3D bioprinter itself.

The connection of a toolhead can require one or a plurality of steps. It may for example involve inserting a nut and/or connecting a cable and/or connecting gas supply.

The 3D bioprinter can also be arranged to display information related to which toolhead should be used and possibly also how it should be prepared.

The 3D bioprinter can be arranged to use one or more exchangeable toolheads together with or not together with one or more non-exchangeable toolheads.

In different embodiments, the base unit processing element is arranged to obtain over the communication interface part information related to characteristics associated to the at least one exchangeable toolhead from the toolhead processing element of the at least one exchangeable toolhead, when the exchangeable toolhead is mounted.

The characteristics associated to the at least one exchangeable toolhead may comprise information related to actuator type such as printing technology of the exchangeable toolhead. The information may define that the exchangeable toolhead is a pneumatic extrusion toolhead, syringe pump toolhead, inkjet toolhead, high temperature extrusion tool head, a tool head for removal of material and/or curing toolhead. The toolhead for removal of material may be a knife and/or a laser toolhead and/or a milling toolhead and/or a drilling toolhead. The curing toolhead may be a light curing toolhead such as UV, visible or laser light. The curing toolhead may by any other type of curing toolhead such as a liquid solution or heat based curing toolhead. The information may define that the at least one exchangeable toolhead is a bio-electrospraying toolhead.

The characteristics associated to the at least one exchangeable toolhead may comprise information related to a sensor technology of the toolhead, said information may define that the toolhead is a camera toolhead, probing toolhead and/or 3D scanning toolhead.

In different embodiments, the base unit processing element is arranged to obtain control signals for control of the at least one exchangeable toolhead based on the information obtained over the communication interface part related to the characteristics of the exchangeable toolhead and to feed the control signals to the communication interface part.

In different embodiments, the 3D bioprinter (1) as defined above further comprises said at least one toolhead having said toolhead processing element (8) and a communication interface part (6) connectable to the communication interface part (5) of the base unit (2). The toolhead processing element of at least one of the toolheads may then be arranged at least partly control operation of said toolhead.

In different embodiments, the 3D bioprinter further comprises a pressurized gas interface part for supply of pressurized gas to the at least one toolhead and/or a light interface part for transmission of light to the at least one toolhead.

In different embodiments, the 3D bioprinter further comprises an exhaust for exhausting gas such as air in a printing space. The exhaust may be implemented in the at least one toolhead.

The base unit processing element (7) is in different embodiments arranged to control the exhaust of gas.

The present disclosure relates further to a 3D bioprinter as defined above, for use in printing constructs that are suitable for use in any application for which a 3D bioprinted construct can be used, such as any one of the applications chosen from: implants in the animal or human body, such as repairing or replacing tissue, topical applications, cosmetic applications, drug discovery, drug test applications or as a disease model, or for other purposes such as various research, investigating or developmental purposes in the pharmaceutical, medical, chemical, personal care, skin care or cosmetic industry, or any other industry for which 3D bioprinted constructs may be of use. The printed constructs comprise a suitable solid, semi-solid or fluid bioink material, and may or may not comprise living cells, depending on the application.

The present disclosure further relates to a 3D bioprinter system comprising a base unit comprising a support adapted mounting of a toolhead, a communication interface for communication with the toolhead, when mounted, and a base unit processing element adapted to communicate with the toolhead over said communication interface (5), and at set of toolheads each toolhead having a communication interface part connectable to the communication interface part of the base unit.

At least one of the toolheads may comprise a toolhead processing element. The toolhead processing element may be arranged to communicate with the base unit processing element.

The present disclosure further relates to a 3D bioprinter toolhead. The 3D bioprinter toolhead is connectable to mechanical interface part of a 3D bioprinter. The 3D bioprinter toolhead further comprises a toolhead processing element and a communication interface part connectable to a communication interface part of the 3D bioprinter.

The toolhead processing element of the 3D bioprinter toolhead may be arranged to store information related to characteristics associated to the at least one toolhead.

The characteristics associated to the at least one exchangeable toolhead may comprise information related to the actuator type such as printing technology of the exchangeable toolhead. The information may define that the exchangeable toolhead is a pneumatic extrusion toolhead, syringe pump toolhead, inkjet toolhead, high temperature extrusion tool head, a tool head for removal of material and/or a curing toolhead. The information may define that the at least one exchangeable toolhead is a bio-electrospraying toolhead The characteristics associated to the at least one exchangeable toolhead may comprise information related to a sensor technology of the toolhead, said information may define that the toolhead is a camera toolhead, probing toolhead and/or 3D scanning toolhead.

The toolhead processing element may be arranged to at least partly control operation such as extrusion control and/or extrusion material temperature control and/or extrusion material viscosity control and/or gas supply control.

The toolhead processing element may be arranged to at least partly control operation of the tool head based on information obtained by sensors arranged at or integrated within the tool head and/or based on information received via the communication interface part.

The toolhead processing element may be arranged to at least partly control operation of the based on information related to material properties such as viscosity and/or temperature, and/or based on information related to nozzle diameter used to extrude.

The toolhead processing element of the toolhead may be arranged to at least partly monitor operation such as monitoring of extrusion material temperature and/or extrusion material level and/or extrusion material viscosity and/or ambient light and/or exhaust gas monitoring and/or wherein the toolhead processing element is arranged to perform data collection and to report via the communication interface part monitoring of the operation and/or wherein the toolhead processing element is arranged to perform error detection and to report said error via the communication interface part.

The present disclosure further relates to a method for bioprinting a construct. The method comprises the steps of
  selecting a bioprinter toolhead having desired characteristics,
    wherein the bioprinter toolhead may have a toolhead processing element storing information related to the characteristics of the bioprinter toolhead,
    wherein the bioprinter toolhead is connectable to a mechanical interface part of the base unit of a bioprinter and
    wherein the bioprinter toolhead has a communication interface part connectable to a communication interface part of the base unit of the bioprinter,
  mechanically and communicatively connecting the selected bioprinter toolhead to the base unit of the bioprinter by means of the interface parts, and activating printing of the construct by providing an activation signal to the base unit processing element of the bioprinter or the toolhead processing element of the toolhead, whereupon printing is performed based on the information related to the characteristics of the bioprinter toolhead stored by the toolhead processing element or manually input by means of a user interface.

In different embodiments, the method further comprises a step of feeding information related to characteristics of the construct to be printed to the base unit processing element or toolhead processing element, wherein printing is performed also based on the information related to characteristics of the construct.

In different embodiments of the method, the printing of the construct is performed by extruding bioink from the toolhead.

In different embodiments, the method for bioprinting a construct comprises a step of exposing the construct to curing such as UV curing after extrusion of bioink.

The present disclosure further relates to a 3D bioprinted construct manufactured by the method as defined above, said construct being made of a bioink material, wherein the bioink material comprises a fluid, semi-solid or solid composition or a combination thereof. The bioink material can be of many different types, and e.g. alginate-based, gelatine-based, collagen-based, silica-based, cellulose-based, polycaprolactone and/or polylactic acid bioinks and/or thermoplastic materials may be used.

In different embodiments, the bioink material comprises living cells.

The 3D bioprinted construct provided by the bioprinter of the present invention typically is a robust and stable structure that is biocompatible and, for some applications, has the ability to become vascularized.

The present disclosure further relates to a 3D bioprinter comprising a base unit having a support adapted for mounting of at least one exchangeable tool head, a communication interface part for communication with the at least one toolhead, when mounted, and a base unit processing element adapted to communicate with the least one toolhead over said communication interface part.

The present disclosure further relates to a 3D bioprinter comprising a base unit having a support adapted for mounting of at least one tool head, a communication interface part (5) for communication with the at least one toolhead, an exhaust for exhausting gas such as air in a printing space, wherein the exhaust may be implemented in the at least one toolhead, and a base unit processing element adapted to communicate with the least one toolhead over said communication interface part and adapted to control the exhaust.

BRIEF DESCRIPTION OF THE DRAWINGS

FIG. 3 is a system overview for example for a 3D bioprinter as disclosed in relation to FIG. 1 or 5 or a 3D printer system as disclosed in relation to FIG. 2.

FIG. 4 is a flow chart schematically disclosing an example of a method for bioprinting a construct.

FIG. 5 discloses schematically a 3D bioprinter according to a third example.

DETAILED DESCRIPTION

Bioprinting, an additive manufacturing technology, has gained due attention for its ability to spatially control the placement of cells, biomaterials and biological molecules. Consequently, it offers endless possibilities to the future of tissue and organ regeneration, basic research and drug screening.

The 3D bioprinter is able to dispense materials while moving in X, Y, and Z directions. This enables the engineering of complex structures from the bottom up. Moreover, this technology allows the biofabrication of biomimetic-shaped 3D structures unique to the target tissue or organ, since it can be combined with CAD/CAM technology using patients' medical images. In a pre-bioprinting process, a model for use by the 3D bioprinter is created. Further, materials that will be used are chosen. Common technologies used for bioprinting are computed tomography (CT) and magnetic resonance imaging (MRI). To print with a layer-by-layer approach, tomographic reconstruction can be done on the images. The now-2D images can then be used by the printer.

Figure 1:
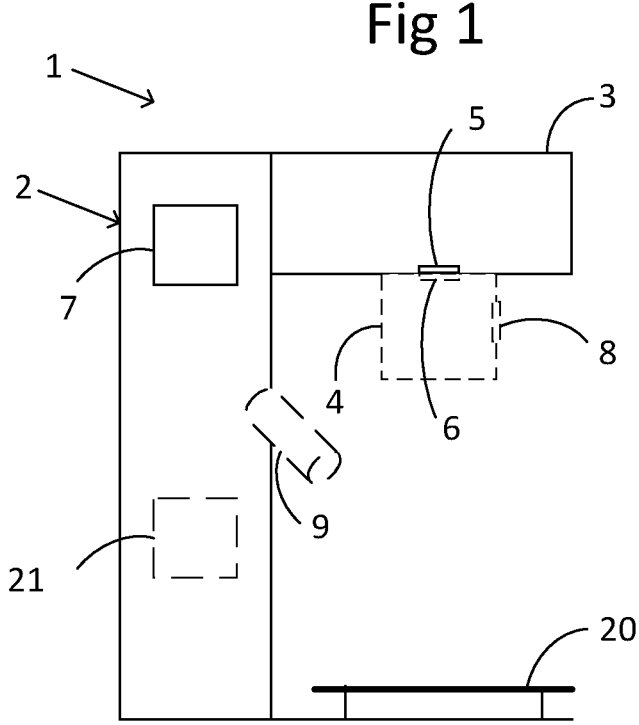
FIG. 1 discloses schematically a 3D bioprinter according to a first example.

FIG. 1 discloses an example of a 3D bioprinter 1. The 3D bioprinter can be used for manufacture of three-dimensional engineered biological tissues. The 3D bioprinter 1 may be used in printing constructs that are suitable for use in any of the applications chosen from: implants in the animal or human body, such as repairing or replacing tissue, topical applications, cosmetic applications and drug test applications.

The 3D bioprinter 1 comprises a base unit 2. The base unit 2 comprises a support 3 adapted for mounting of at least one toolhead 4. In one example the support 3 is adapted to accommodate a plurality of toolheads 4.

In one example, the support 3 is adapted for mounting of at least one exchangeable toolhead 4. The exchangeable toolhead(s) can then be dismounted and displaced with other toolhead(s). In one example, the support 3 is adapted for mounting of at least one non-exchangeable toolhead. In one example, the support may be adapted for mounting of at least one exchangeable toolhead and at least one non-exchangeable toolhead 4.

In the example where the support 3 is adapted for mounting of at least one exchangeable toolhead, the 3D bioprinter becomes very flexible and efficiency in operation of the 3D bioprinter can be increased. For example, the user can prepare the toolhead outside the 3D bioprinter, wherein the preparation may for example involve loading material and/or selecting needle. Then the currently used toolhead can be substituted with the one currently used.

Thereby the bioprinter does not need to be stopped for time consuming activities such as loading of material and/or changing needle. Instead, a short stop can be made to substitute the currently used toolhead with the prepared one. Alternatively, the currently used toolhead can be exchanged when printing. For example, if the support 3 is adapted to mount a plurality of toolheads, the exchange can easily be done while printing.

The toolhead can be inserted or removed by user with our without use of a tool. Alternatively, the toolhead can be automatically inserted and/or removed by the 3D bioprinter itself.

The connection of a toolhead can require one or a plurality of steps. It may for example involve inserting a nut and/or connecting a cable and/or connecting gas supply.

The at least one toolhead 4 may include at least one actuating toolhead and/or at least one sensor toolhead. The actuating toolhead may be provided with sensor(s). Examples of actuating toolheads include pneumatic extrusion toolheads, syringe pump toolheads, inkjet toolheads, high temperature extrusion tool heads, tool heads for removal of material, curing toolheads, and/or bio-electrospraying toolheads. The toolheads for removal of material may comprise a knife and/or a laser toolhead and/or a milling toolhead and/or a drilling toolhead. The curing toolheads may comprise a curing UV toolhead and/or a visible light curing toolhead and/or a laser light curing toolhead. Other examples of actuating toolheads include exhaust gas toolheads for exhaust of gas such as air.

Examples of sensing toolheads include camera toolheads, probing toolheads and/or 3D scanning toolheads.

The base unit 2 further comprises a communication interface part 5 for communication with the at least one toolhead, when mounted. The communication may involve communication of control signals for control of the toolhead. The communication may involve communication of sensor signals from the toolhead. Information which can be communicated between the base unit and toolhead will be discussed more in detail later.

The toolhead 4 comprises a corresponding communication interface part (6) connectable to the communication interface part (5) of the base unit (2). The toolhead 4 may also comprise a toolhead processing element 8.

The communication interface parts 5, 6 may be arranged for analog and/or digital communication. The communication interface parts may form a wired interface or a contact-less interface (non-wired interface). The communication interface may for example comprise an electrical interface, and/or light interface and/or audio interface and/or a radio interface. Communication over the interface part may be performed in accordance with any communication protocol.

The base unit 2 further comprises a base unit processing element 7. The base unit processing element may be adapted to communicate with the toolhead processing element 8 of the at least one toolhead 4 over said communication interface parts 5, 6. In an alternative example, toolhead is not provided with a toolhead processing element arranged to communicate with base unit processing element.

The base unit processing element 7 and the toolhead processing element 8, if present, have storing capacity. The base unit processing element 7 and toolhead processing element 8, if present, are capable transmitting and/or receiving analog or digital data. At least one of the base unit processing element 7 and toolhead processing element 8 has processing capacities so as to perform calculations.

When the toolhead 4 has a toolhead processing element 8, the need for manual user input related to the toolhead can be reduced or eliminated. The possible burdensome manual user input which can be avoided/reduced includes for input of example type, dimension, and other characteristics of the toolhead. This makes it easier and fasted to use the 3D bioprinter. The automated retrieval of data related to the toolhead further removes the risk of manual input of erroneous information related to the toolhead.

In accordance with this example where the toolhead has data storing capacity, the toolhead processing element may be arranged to store information related to characteristics associated to the at least one exchangeable toolhead. The characteristics associated to the at least one exchangeable toolhead may comprise information related to actuator type such as printing technology of the exchangeable toolhead. The information may define that the exchangeable toolhead is a pneumatic extrusion toolhead, syringe pump toolhead, inkjet toolhead, high temperature extrusion tool head, a tool head for removal of material, a curing toolhead and/or a bio-electrospraying toolhead. The information may define that the exchangeable toolhead for removal of material is be a knife, a laser toolhead, a milling toolhead and/or a drilling toolhead. The information may define that the exchangeable curing toolhead may be a curing UV toolhead, a visible light curing toolhead or a laser light curing toolhead.

The characteristics associated to the at least one exchangeable toolhead may comprise information related to a sensor technology of the toolhead, said information may define that the toolhead is a camera toolhead, probing toolhead and/or 3D scanning toolhead.

The base unit processing element may be arranged to obtain over the communication interface part information related to characteristics associated to the at least one exchangeable toolhead from the toolhead processing element of the at least one exchangeable toolhead, when the exchangeable toolhead is mounted.

The toolhead processing element 8, when present, may be arranged to collect data related to the toolhead, for example obtained by the toolhead itself or sensors integrated within the toolhead, mounted thereon and/or in association therewith. The toolhead processing element can then be arranged to format the collected data to a format appropriate for the 3D bioprinter, i.e. in accordance with set protocol for communication with the base unit 2. The toolhead processing element can further be arranged to transmit the data in the appropriate format to the communication interface part of the 3D bioprinter. This facilitates integration between the 3D bioprinter base unit 2 and toolhead. This is particularly advantageous for exchangeable toolheads.

When both the base unit 2 and at least one of the toolheads 4 have processing capacity, processing for control of operation of the toolheads can be performed either by the toolhead processing element(s) 8 or the base unit processing element 7. In an alternative example, the processing capacity of both the base unit processor 7 and at least one of the toolhead processing element(s) 8 are used for control of operation of the toolheads. In accordance with this example, either the base unit processing element 7 or at least one of the toolhead processing elements 8 is/are acting as master processor and the other processor(s) are acting as slave processor, or vice versa.

Thus, the base unit processing element and/or toolhead processing element is arranged to obtain control signals for control of the at least one exchangeable toolhead based on the information related to the characteristics of the exchangeable toolhead and to feed the control signals to the toolhead for control for the toolhead.

Thus, the toolhead processing element(s) 8 may have processing capacities which in one example is used to at least partly control operation of its toolhead or other equipment such as another toolhead and/or an exhaust for gas. One advantage with implementing this functionality at the toolhead processing element(s) 8 is that software within the base unit 2 may not need to be amended and updated, or at least only minor updates are necessary, when updated toolheads are mounted to the 3D bioprinter. Thus, an existing 3D bioprinter may be upgraded with new toolhead technologies substantially without amending the software of the base unit.

The base unit processing element and/or toolhead processing element(s) may be arranged to at least partly control operation such as extrusion control and/or extrusion material temperature control and/or extrusion material viscosity control and/or gas supply control.

The base unit processing element and/or toolhead processing element(s) may be arranged to at least partly control operation of the toolhead based on information obtained by sensors arranged at or integrated within the tool head and/or based on information received via the communication interface part.

The base unit processing element and/or toolhead processing element(s) may be arranged to at least partly control operation of the based on information related to material properties such as viscosity and/or temperature, and/or based on information related to nozzle diameter used to extrude.

The toolhead processing element of the toolhead and/or base unit processing element may be arranged to at least partly monitor operation such as monitoring of extrusion material temperature and/or extrusion material level and/or extrusion material viscosity and/or ambient light and/or exhaust gas monitoring and/or wherein the toolhead processing element is arranged to perform data collection and to report via the communication interface part monitoring of the operation and/or wherein the toolhead processing element is arranged to perform error detection and to report said error via the communication interface part.

The 3D bioprinter comprises further in the illustrated example an optional exhaust 9 for exhausting gas such as air in a printing space. This is described more in detail in relation to FIG. 5.

The exhaust 9 may be implemented in the at least one toolhead. The 3D bioprinter 1 may then comprise a pressurized gas interface part (not illustrated) for supply of pressurized gas to the at least one toolhead.

The base unit processing element (7) or one toolhead processing element is on one example arranged to control the exhaust of gas. This is described more in detail in relation to FIG. 5.

The 3D bioprinter 1 may comprise a light interface part for transmission of light to the at least one toolhead.

Further, the 3D bioprinter 1 has a user interface 21 arranged for user input and/or display of information.

Further, the 3D bioprinter 1 has a receiving surface 20 on which the construct is arranged to be formed.

Figure 2:
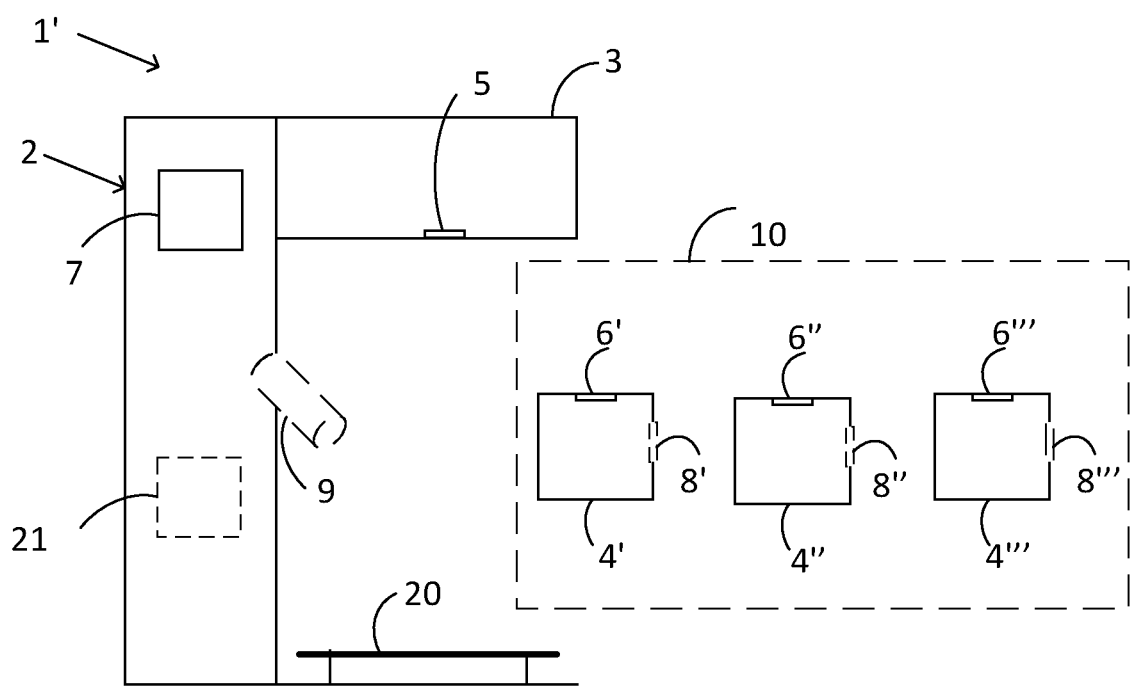
FIG. 2 discloses schematically a 3D bioprinter system according to a second example.

In FIG. 2, an example of a 3D bioprinter system 1' is disclosed. As disclosed in relation to FIG. 1, the 3D bioprinter system comprises a base unit 2 comprising a support 3 adapted mounting of at least one toolhead 4', 4", 4'''. The base unit 2 comprises further a communication interface part 5 for communication with the toolhead, when mounted. The base unit comprises further a base unit processing element 7 adapted to communicate with the at least one toolhead over said communication interface 5.

The 3D bioprinter system 1' comprises further a set 10 of toolheads 4', 4", 4'''. Each toolhead has a communication interface part 6', 6", 6''' connectable to the communication interface part '5 of the base unit 2.

At least one of the toolheads may comprise a toolhead processing element 8', 8", 8'''. The toolhead processing element is arranged to communicate with the base unit processing element.

The 3D bioprinter system 1" as disclosed in relation to this figure may have one or more of the additional features as disclosed in relation to the FIGS. 1, 3 and 4, and 5.

In FIG. 3, an example of a system overview of a system for 3D bioprinting is disclosed. The system comprises a 3D bioprinter part 1. The 3D bioprinter part comprises a base unit processing element 7. The base unit processing element 7 may be designed as discussed in relation to the other figures. The 3D bioprinter part may also comprise a user interface 21. The user interface 21 may be designed as discussed in relation to the other figures.

The 3D bioprinter part 1 may also comprise one or a plurality of base unit actuators or sensors 13. The base unit actuators or sensors 13. may comprise a positioning system for performing 3D printing. Positioning systems for use in 3D bioprinters are known in the art and will not be discussed in detail herein. Generally speaking, the positioning system allows for dispense of materials while moving in X, Y, and Z directions. The base unit actuators or sensors 13 may comprise a pressurized gas supply system, as disclosed herein in relation to the other figures. The base unit actuators or sensors 13 may comprise temperature sensors and/or bed heating/cooling and/or humidity control in the chamber and/or temperature control in the chamber and/or light control and/or sterilization control.

The system also comprises communication interface as discussed in relation to the other figures. Further the support part 3 of the bioprinter is in the illustrated example formed with a base unit mechanical interface 13 and the toolheads 4', 4" are provided with corresponding mechanical toolhead interfaces 14', 14".

The toolheads 4', 4" comprise further toolhead processing elements 8', 8". The toolhead processing elements 8', 8" may be designed as discussed in relation to the other figures. The toolheads 4', 4" comprise further toolhead actuator or sensors 12', 12". The toolhead actuator or sensors 12', 12" are controlled by the toolhead processing elements 8', 8" or base unit processing element 7. This has been discussed in in relation to the other figures.

In FIG. 4, a method 40 for bioprinting a construct is illustrated. The method comprises a step S2 of selecting a toolhead having desired characteristics. The bioprinter toolhead may have a toolhead processing element storing information related to the characteristics of the bioprinter toolhead. The bioprinter toolhead is connectable to a mechanical interface part of the base unit of a bioprinter. The bioprinter toolhead has a communication interface part connectable to a communication interface part of the base unit of the bioprinter. The 3D bioprinter can also be arranged to display or in any other way present information related to which toolhead should be used and possibly also how it should be prepared. I.e. in accordance with this example, the 3D printer is arranged to provide decision support. The 3D bioprinter may be arranged to provide the decision support based on status parameter(s) related to operation and/or characteristics of the construct(s) to be printed or which is printed. The status parameter(s) and/or characteristics of the construct(s) to be printed is available at the base unit processing element and/or one or more toolhead processing element.

In a next step S3, the selected bioprinter toolhead is mechanically and communicatively connected to a base unit of the bioprinter by means of the interface parts. This step may be performed either manually or automatically.

In a next step S4, printing of the construct with the connected toolhead is activated by providing an activation signal to the base unit processing element of the bioprinter or the processing element of the toolhead. Printing is then performed based on the information related to the characteristics of the bioprinter toolhead stored by the processing element or manually input by means of a user interface. The printing of the construct may be performed by extruding bioink from the toolhead. Detection of a new printhead can be done automatically by the 3D bioprinter or it can be set by the user. The printing may be activated manually or automatically by the 3D bioprinter.

The method may further comprises a step S1 of feeding information related to characteristics of the construct to be printed to the base unit processing element or processing element before printing is activated. Printing may then be performed also based on the information related to characteristics of the construct. In the illustrated example, this step is performed before selection of a toolhead. This has the advantage that decision support in selecting toolhead and/or it can be provided.

The method for bioprinting a construct may further comprise a step S5 of exposing the construct to curing after extrusion of bioink. In this step one of the toolheads may be used. This step may be initiated manually or automatically. The curing may be a light curing such as UV, visible or laser light. The curing may be performed using any other method such curing with a liquid solution or heat based curing.

A 3D bioprinted construct manufactured by the method as defined above, may be made of a bioink material, wherein the bioink material comprises a fluid, semi-solid or solid composition or a combination thereof. The bioink material may comprise living cells.

In FIG. 5, an example of a 3D bioprinter 1" is disclosed. The 3D bioprinter 1" comprises a base unit 2 having a support 3 adapted for mounting of at least one tool head 4. The base unit 2 further comprises a communication interface part 5 for communication with the at least one toolhead. The 3D bioprinter 1''' comprises further an exhaust 9 for exhausting gas such as air in a printing space. In the illustrated example, the exhaust 9 is mounted at the base unit 2. However, it can instead for example be implemented in the at least one toolhead. The exhaust is connected to a gas supply arrangement (not illustrated). This is for example in practice achieved by connecting the exhaust 9 to a gas supply arrangement comprising a pump, an accumulator and digitally or analogically controlled pressure regulators. In using a digitally controlled and monitored pump, the pump usage can be adapted to the amount of air to be used for the specific bioprint. This allows for the pump to be used less. Further, this has the advantage that a more silent operation is achieved.

In one example, the gas supply arrangement is accommodated in the 3D bioprinter 1". The user does not need to supply pressurized gas such as air the. This enables for a more portable and easy to use 3D bioprinter arrangement.

The 3D bioprinter 1" comprises further a control or processing element adapted to control the exhaust. Thereby, the base unit processing element can be adapted to control the supply arrangement based on the requirements or requests associated to the specific print. Thus, control or processing element is arranged to adapt the use of exhaust gas to the situation without the need of manual input. The control or processing element may be arranged to control the exhaust based also on sensor data such as data related to environment temperature and/or environment humidity and/or extruder material temperature and/or extruder material viscosity and/or other characteristics of the extruder material.

In the illustrated example, a base unit processing element 7 is arranged at the base unit. The base unit processing element can then be arranged to control the exhaust 9. However, the control or processing element controlling the exhaust can be formed anywhere as long there is communication for control. For example, the control or processing element can be at least partly performed at a toolhead processing element.

In the illustrated example, the base unit processing element 7 and/or toolhead processing element(s), if any, is further arranged to control the operation of the at least one tool head. The 3D bioprinter 1" as disclosed in relation to this figure may have one or more of the additional features as disclosed in relation to the FIGS. 1, 2, 3 and 4.

Application Example—Bioprinting of Cell-Laden Bioink into Auricular and Lattice Structures A 3D model of a human auricle reconstructed from an MRI scan was used for the bioprinting experiment. The STL (STereoLithography) file of the auricular model was processed in the slicing software Slic3r. First, the model was scaled to 35% of the original size, the theoretical porosity of the auricular model was set to 50%, and the G-code file for the 3D bioprinter was generated. This bioprinter is equipped with dual pneumatic-driven extruders to build complex 3D structures using two different bioinks and cell types simultaneously. It also comes with a UV curing system (e.g. 365 nm and 405 nm wavelength) for crosslinking photo-curable bioinks. Chondrocyte-laden NFC-A hydrogel constructs were bioprinted in the shape of a human auricle using a pneumatic-driven extruder. After bioprinting, the cell-laden hydrogel constructs were immediately crosslinked with 100 mM aqueous $CaCl_2$ solution for 10 min and then rinsed and incubated in culture medium in standard culture conditions (37° C., 5% $CO_2$ and 95% relative humidity).

The invention claimed is:

1. A 3D bioprinter comprising a base unit,
   the base unit comprising a support adapted for mounting of a plurality of toolheads, wherein the support comprises a support part comprising a plurality of toolhead mounts, each adapted for mounting of an exchangeable toolhead,
   the base unit further comprising a communication interface part for communication of data with each mounted toolhead, the communication interface part being on or internal to the support on which at least one of the plurality of toolheads may be mounted, and
   the base unit further comprising a base unit processing element on or internal to the base unit and adapted to communicate with a toolhead processing element of a mounted toolhead over said communication interface part,
   wherein the base unit processing element is arranged to obtain over the communication interface part information related to a mounted exchangeable toolhead from a toolhead processing element of the mounted exchangeable toolhead, and perform the process of controlling the operation of the mounted exchangeable toolhead at the support based on the obtained information, when the exchangeable toolhead is mounted on the support of the base unit,
   wherein the plurality of exchangeable toolheads comprise information related to at least one of
      I.) an actuator type such as printing technology of the exchangeable toolhead, said information defining that the exchangeable toolhead is a pneumatic extrusion toolhead, syringe pump toolhead, inkjet toolhead, high temperature extrusion tool head, a tool head for removal of material and/or curing toolhead, or
      II) a sensor technology of the toolhead, said information defining that the exchangeable toolhead is a camera toolhead, probing toolhead and/or 3D scanning toolhead,
   and
   wherein the support is adapted to allow an exchange of a toolhead at one toolhead mount during an ongoing actuation at another toolhead mount.

2. The 3D bioprinter according to claim 1, further comprising the mounted exchangeable toolhead having said toolhead processing element connectable to the communication interface part of the base unit.

3. The 3D bioprinter according to claim 2, wherein the toolhead processing element of the mounted exchangeable toolhead is arranged to at least partly control operation of said toolhead.

4. The 3D bioprinter according to claim 1, further comprising a pressurized gas interface part for supply of pressurized gas to the at least one toolhead.

5. The 3D bioprinter according to claim 1, further comprising an exhaust for exhausting gas such as air in a printing space, wherein the exhaust is implemented in the at least one toolhead.

6. The 3D bioprinter according to claim 5, wherein the base unit processing element is arranged to control the exhaust of gas.

7. The 3D bioprinter according to claim 1, for use in printing constructs that are suitable for use in any of the applications chosen from: implants in the animal or human body, such as repairing or replacing tissue, topical applications, cosmetic applications, drug test, drug discovery applications or as a disease model, or for other research, investigating or developmental purposes in the pharmaceutical, medical, chemical, personal care, skin care or cosmetic industry or any other industry for which 3D bioprinted constructs may be of use.

8. The 3D bioprinter according to claim 1, wherein the support is adapted to accommodate at least one exchangeable toolhead and at least one non-exchangeable toolhead.

9. The 3D bioprinter according to claim 1, wherein the base unit processing element is adapted to communicate with the toolhead processing element of the mounted exchangeable toolhead over said communication interface part.

10. The 3D bioprinter according to claim 1, further comprising a light interface part for transmission of light to the at least one toolhead.

* * * * *